(12) United States Patent
Lipowicz

(10) Patent No.: US 7,832,397 B2
(45) Date of Patent: Nov. 16, 2010

(54) AEROSOL POWDER DELIVERY DEVICE

(75) Inventor: Peter John Lipowicz, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 1001 days.

(21) Appl. No.: 11/640,973

(22) Filed: Dec. 19, 2006

(65) Prior Publication Data

US 2007/0175476 A1    Aug. 2, 2007

Related U.S. Application Data

(60) Provisional application No. 60/754,192, filed on Dec. 28, 2005.

(51) Int. Cl.
*A61M 11/00* (2006.01)
(52) U.S. Cl. .............................. 128/203.12; 128/203.15
(58) Field of Classification Search ..................
128/200.11–200.24, 203.12, 203.15; 55/485
See application file for complete search history.

(56) References Cited

U.S. PATENT DOCUMENTS

| 2,642,063 | A | * | 6/1953 | Brown ................ 128/203.15 |
| 4,841,964 | A | | 6/1989 | Hurka et al. |
| 4,995,407 | A | | 2/1991 | Kossiakoff et al. |
| 5,441,060 | A | | 8/1995 | Rose et al. |
| 5,699,789 | A | | 12/1997 | Hendricks |
| 5,746,227 | A | * | 5/1998 | Rose et al. ............. 128/203.15 |
| 6,427,688 | B1 | * | 8/2002 | Ligotke et al. ......... 128/203.15 |
| 6,604,698 | B2 | | 8/2003 | Verhoff et al. |
| 6,681,768 | B2 | | 1/2004 | Haaije de Boer et al. |
| 7,082,943 | B1 | * | 8/2006 | Clark .................. 128/200.23 |
| 2003/0111088 | A1 | | 6/2003 | Fox |
| 2005/0016553 | A1 | | 1/2005 | Iannuzzi |

FOREIGN PATENT DOCUMENTS

| EP | 0324361 A | 7/1989 |
| WO | WO 87/05213 A1 | 9/1987 |
| WO | WO 90/13327 A1 | 11/1990 |
| WO | WO 02/074357 A | 9/2002 |

OTHER PUBLICATIONS

International Preliminary Report on Patentability dated Jul. 10, 2008 for PCT/IB2006/004206.
International Search Report and Written Opinion dated Sep. 24, 2007 for PCT/IB2006/004206.

* cited by examiner

*Primary Examiner*—Steven O Douglas
(74) *Attorney, Agent, or Firm*—Buchanan Ingersoll & Rooney PC

(57) ABSTRACT

An aerosol powder delivery device, a method of producing or delivering aerosol particles, a method of making a delivery device, and an inhaler kit are provided. The device can be used to produce an aerosolizable powder by breaking or deagglomerating the aerosolizable powder into aerosol particles for inhalation. The aerosol particles can be produced by mechanically agitating or shaking a hollow device with the aerosolizable powder and a second powder to mechanically break or loosen aerosol particles from the aerosolizable powder. Thus, a small, lightweight, simple, sealed and stable device without complex moving parts, external power sources or heat is provided to aerosolize powder into aerosol particles for transmucosal delivery into a mouth upon inhalation.

20 Claims, 4 Drawing Sheets

AEROSOL POWDER DELIVERY DEVICE

CROSS REFERENCE TO RELATED APPLICATION

This application claims priority under 35 U.S.C. §119(e) to U.S. provisional Application No. 60/754,192, filed on Dec. 28, 2005, the entire content of which is incorporated herein by reference.

BACKGROUND

Dry powder pharmaceutical inhalers (DPI) are used to deliver pharmaceuticals in aerosol form through inhalation. A DPI typically contains a dry pharmaceutical powder. Upon inhalation action by a patient, the DPI mixes and entrains the pharmaceutical powder in a stream of air in an aerosolized form for delivery to the patient's airways.

A DPI can aerosolize the dry powder by grinding a powder using a brush (see U.S. Pat. No. 5,441,060) or by impacting larger particles within a baffle (see U.S. Pat. No. 5,699,789) for example. However, since DPI devices often require particles on the order of micrometers (about 1 to 5 micrometers for lung deposition) and specific dosing amounts, these DPI devices utilize complicated mechanisms to control aerosol particle sizes and dosage levels.

SUMMARY

An aerosol powder delivery device is provided with an aerosolizable powder, wherein the powder contains a substance for inhalation, and wherein at least a portion of the aerosolizable powder is capable of breaking into aerosol particles for inhalation of the substance. Optionally, the aerosol powder delivery device can shaped to look and feel like a smoking article (e.g., a cigarette), and the substance for inhalation can include flavorants.

Also, one or more filters can be provided, wherein the filters can be used to confine the substance in powder form (hereinafter "aerosolizable powder") within the device. A pair of filters, one upstream and another downstream can be provided to confine the substance within the device, with the downstream filter being capable of passing aerosol particles of the substance through the filter for inhalation. Also, the aerosol powder delivery device can also be provided with a secondary powder, wherein the secondary powder can be used to agitate, impact, and aerosolize the substance in powder form into aerosol particles.

Also provided is an aerosol powder delivery device, comprising: a hollow device; aerosolizable powder adapted to produce aerosol particles within the hollow device, wherein at least a portion of the aerosol particles comprise the same material as the aerosolizable powder; and a secondary powder within the hollow device, wherein at least a portion of the aerosolizable powder, the secondary powder, or both are about 1.0 mm to about 4.0 mm in at least one dimension.

Also provided is a method of producing or delivering aerosol particles, comprising: agitating an aerosolizable powder and a secondary powder in a hollow device to aerosolize the aerosolizable powder into aerosol particles; and passing air through an upstream end of the hollow device so as to remove the aerosol particles from a downstream end of the hollow device.

Also provided is a method of making an aerosol delivery device, comprising: filling a hollow device with an aerosolizable powder and a secondary powder, wherein at least a portion of the secondary powder and the aerosolizable powder are larger than about 1.0 mm in at least one dimension and sealing an upstream portion and a downstream portion of the hollow device using filters, wherein the aerosolizable powder and the secondary powder are confined within the hollow device between the filters.

Also provided is an aerosol delivery device kit of component parts capable of being assembled, comprising: a hollow device; powder including an aerosolizable powder adapted to produce aerosol particles within the hollow device, wherein at least a portion of the aerosol particles comprise smaller particles of the same material as the aerosolizable powder, and a secondary powder within the hollow device, wherein at least a portion of the aerosolizable powder, the secondary powder, or both are at least about 1.0 mm in at least one dimension, wherein the powder is adapted to be positioned within the hollow device; and upstream and downstream filters, whereby the upstream and downstream filters may be positioned on the upstream and downstream end portions, respectively, of the hollow device to contain the powder within the hollow device.

BRIEF DESCRIPTION OF THE DRAWING FIGURES

DETAILED DESCRIPTION

An aerosol powder delivery device is provided, wherein aerosolizable powder is contained in a hollow device for aerosolization into aerosol particles for inhalation. In order to aerosolize the aerosolizable powder, the hollow device can be mechanically agitated by a consumer to deagglomerate or break up the aerosolizable powder into aerosol particles. The deagglomeration or breaking up of the aerosolizable powder can occur by impacting powder particles against other powder particles or against walls of the hollow device.

Figure 1:
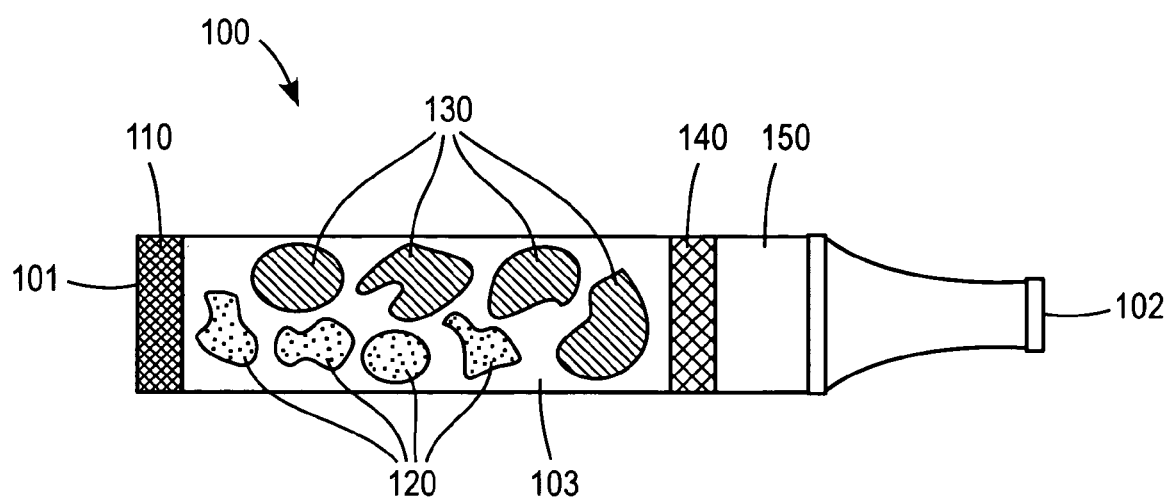
FIG. 1 illustrates an embodiment of an aerosolizable powder delivery device.

An exemplary embodiment of an aerosol powder delivery device 100 is provided in FIG. 1. In FIG. 1, the aerosol powder delivery device 100 is a hollow device, hollow, elongated device, or tube which includes an upstream filter 110, an aerosolizable powder 120, a secondary powder 130, a downstream filter 140, and an optional secondary filter 150, which can be located near an optional mouthpiece (illustrated in FIG. 1 at the downstream end 102 of the device 100).

As provided in FIG. 1, the aerosol powder delivery device 100 can be used to aerosolize the aerosolizable powder 120 by agitating the aerosolizable powder 120 with the secondary powder 130 within a cavity 103 of the device 100. By agitating the device 100, the aerosolizable powder 120 moves within the device causing the aerosolizable powder 120 to impact against itself, the secondary powder 130, and/or the walls and filters 110, 140 of the device 100, such that the aerosolizable powder 120 can form aerosol particles for inhalation.

In one exemplary embodiment illustrated in FIGS. 1 and 2A-2D, the powder pieces of the aerosolizable powder 120 can be approximately the same initial size as the secondary powder 130. In another exemplary embodiment, as illustrated in FIGS. 3A and 3B, aerosolizable powder 310 can be smaller than the secondary powder 130, on the order of aerosol particles 320, wherein secondary powder 130 can be provided to break up agglomerations 330 of the small aerosolizable powder 310 to aerosolize the aerosolizable powder 310 into aerosol particles 230, which can be filtered and ejected as filtered aerosol particles 320.

Figure 2A:
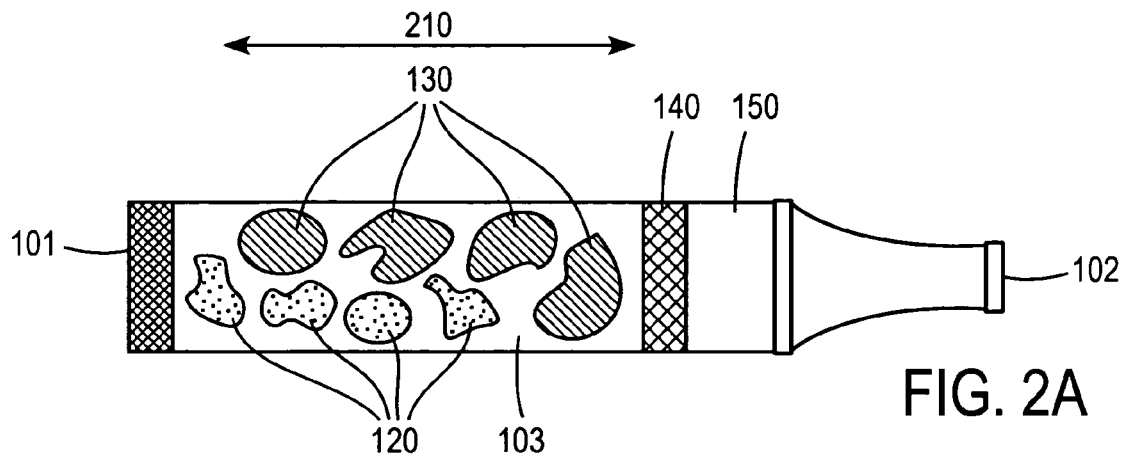
FIGS. 2A-2D illustrate an exemplary embodiment of a method of aerosolizing a powder for inhalation.
Figure 3A:
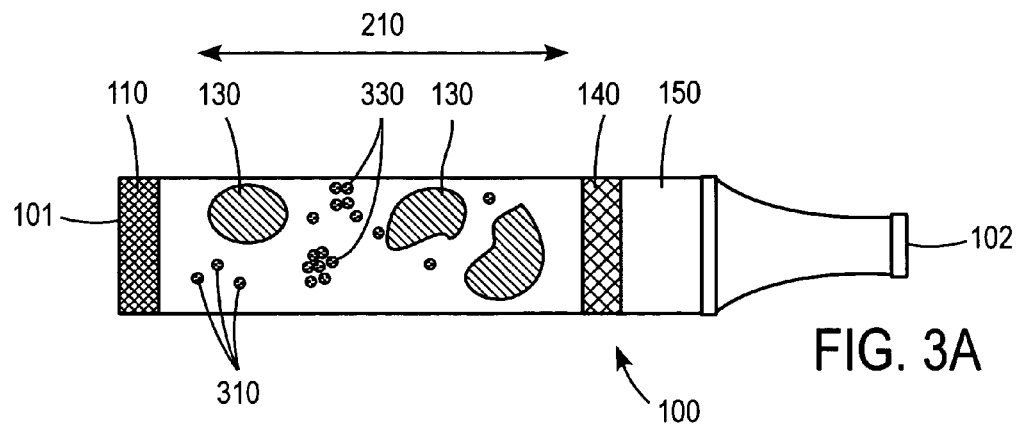
FIGS. 3A-3C illustrate another exemplary embodiment of a method of aerosolizing a powder for inhalation.

For example, as illustrated in FIG. 2A (and similarly in FIG. 3A), the device 100 can be mechanically shaken by a consumer. This shaking causes the aerosolizable powder 120 to impact with each other, as well as the secondary powder 130, the walls of the device 100, the upstream filter 110, and the downstream filter 140 to form aerosol particles as illustrated in FIG. 2A. Preferably, as illustrated in FIG. 2A (and FIG. 3A), the device 100 is shaken in an axial direction 210.

Figure 2B:
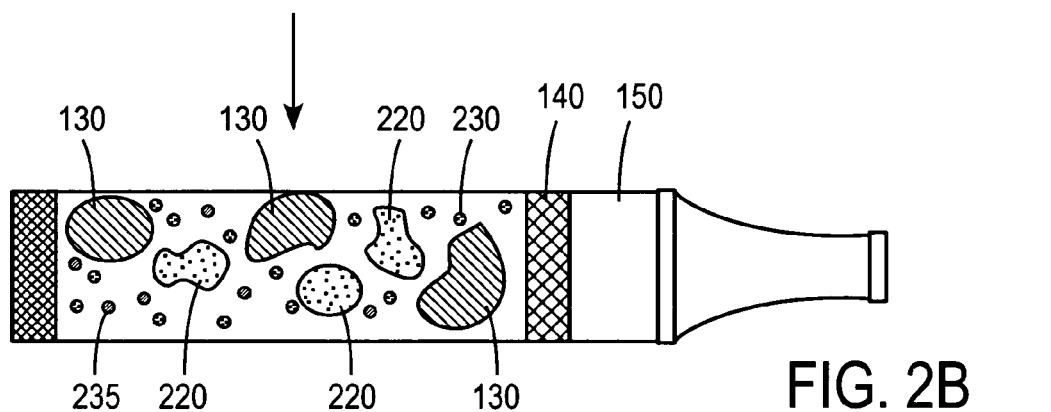

As a result of the impact, as illustrated in FIG. 2B, the aerosolizable powder 120 can be broken up to form both smaller aerosolizable powder pieces 220 and aerosol particles 230. As illustrated in FIG. 2B, the aerosolizable powder 120 can include larger, solid particles. Alternatively, as illustrated in FIG. 3A, the aerosolizable powder 120 can include aerosol particles or smaller aerosolizable powder 310 separately, or in agglomerations 330 of aerosolizable powder 310.

Figure 3B:
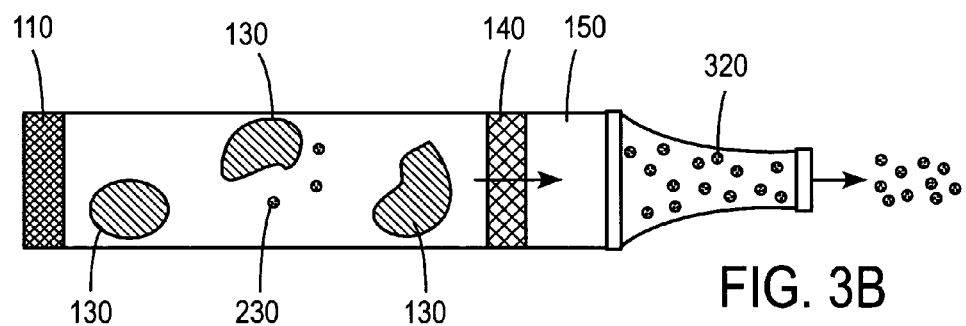

It is noted that secondary powder 130 can be used to break or deagglomerate aerosolizable powder 220, 130 (i.e., similar to a ball mill), as illustrated in FIGS. 2B and 3B, and/or the secondary powder 130 can itself be broken to form optional secondary aerosol particles 235, as illustrated in FIG. 2B.

Figure 3C:
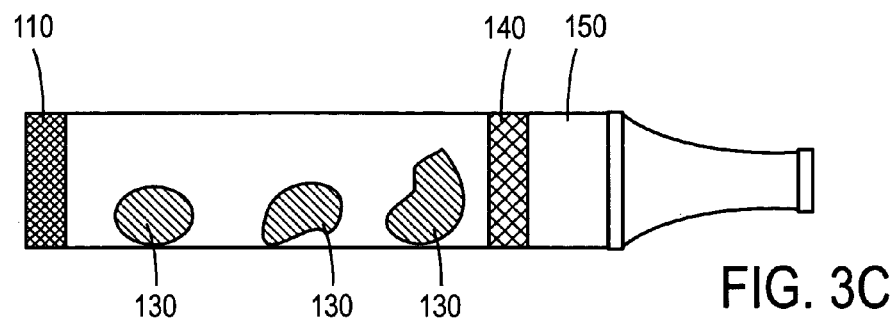

If the secondary powder 130 forms secondary aerosol particles 235, as illustrated in FIG. 2B, the secondary aerosol particles 235 can be used to alter the characteristics of the resultant aerosol provided for inhalation. Alternatively, the secondary powder 130 can be non-aerosolizable and/or can remain unbroken and maintain its original size, as illustrated in FIGS. 3B, and 3C.

Figure 2C:
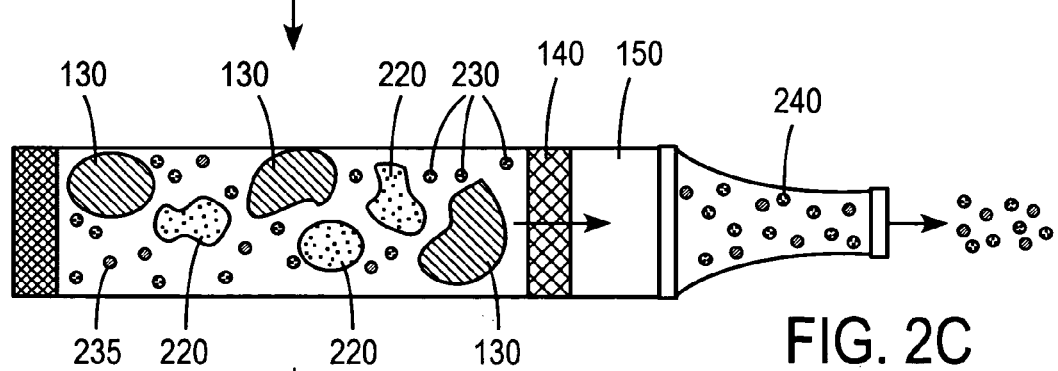

As illustrated in FIG. 2C, the aerosol particles 230 can be inhaled after passing through the downstream filter 140, wherein the aerosolizable powder 120, 220 and the secondary powder 130 can be blocked by the downstream filter 140, while allowing filtered aerosol particles 240 to pass therethrough. Additionally, an optional secondary filter 150 can be provided to further control the sizes of the aerosol particles passing therethrough, wherein secondary filtered aerosol particles can be further tailored to a predetermined size range and distribution for inhalation.

Figure 2D:
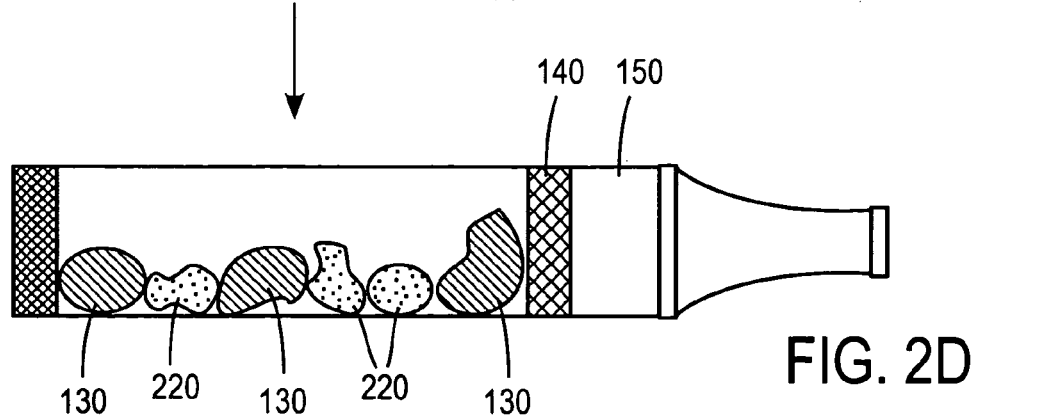

After single use, as illustrated in FIG. 2D, the device 100 can include smaller aerosolizable powder pieces 220, as a result of reduction in aerosolizable powder 220 mass due to the formation of the aerosol particles 240 (FIG. 2C) therefrom. Alternatively, the device 100 can include only secondary powder 130 if the aerosolizable powder is exhausted, as illustrated in FIG. 3C. It is noted that the device 100 can be disposed after single use or can be reused as long as the aerosolizable powder pieces 220 is available to continue to yield aerosol particles 230.

In order for a consumer to determine re-usability of the device 100, an indicator can be provided to signal the consumer of the level of powders remaining. It is noted that any electronic, mechanical or visual indicator can be used, but preferably, the indicator is one ore more visually clear windows on the outer walls of the device 100, such that the indicator does not substantially increase the mass, weight or complexity to the device 100.

Additionally, the device 100 can be disposable or refillable. In an exemplary embodiment of a refillable device, the upstream filter can be removed and the hollow device can be either fully or partially refilled. Alternatively, means for refilling, such as a replaceable cartridge, can be provided to refill the device 100 without removal of the upstream filter. In an exemplary embodiment, the device 100 can be opened through a latch located on a circumferential area of the device 100 or the device 100 can be opened (i.e., twisted in the axial, radial, or circumferential direction to separate one portion of the device from another) for refilling.

By providing the device 100 as described herein, a simple, mechanical inhaler, which forms aerosol particles through mechanical movement or agitation by a consumer and thus without liquids, complex moving parts, external energy and/or heat, can be provided for aerosol particles to be delivered into the mouth and not the lower airways of the lungs. Additionally, a delivery device that is small, lightweight, sealed, and stable is therefore available.

In order to use the device 100 provided herein, the aerosol powder delivery device includes an upstream end 101, where air enters the device 100 through the upstream filter 110 and passes to a downstream end 102, wherein filtered aerosol particles 240, 320 exit from the device, as illustrated in FIGS. 2C and 3B.

Toward the upstream end 101, an upstream filter 110 can be provided. In an exemplary embodiment, the upstream filter 110 is provided to allow air into the device 100, while containing and preventing escape of the powder from the device 100 and controlling a resistance to draw (RTD) if desired. The upstream filter 110 can be any material or shape capable of allowing entrainment air to pass through, while also preventing the powders from escaping. Exemplary embodiments of materials which can be used as the upstream filter 110 include but are not limited to polymeric foams, honeycomb filters, screens, such as fine metal mesh screens, or cigarette filter material, such as cellulose acetate. Preferably, the upstream filter 110 also is capable of providing radial and axial integrity to the device 100, such that the device 100 can maintain its predetermined shape in ordinary use.

Additionally, a downstream filter 140 can be provided on a downstream portion of an aerosol powder delivery device 100. Similar to the upstream filter 110, the downstream filter 140 is provided to contain the powders within the device 100; however, the downstream filter can be provided to also allow aerosolized particles to pass therethrough (along with entrainment air) for inhalation. Exemplary embodiments of materials which can be used as the downstream filter 140 include but are not limited to polymeric foams, honeycomb filters, screens, such as fine metal mesh screens, or cigarette filter material, such as cellulose acetate.

In addition to the downstream filter 140, an optional secondary filter can also be provided within a downstream area 150 of the device to allow a predetermined amount of aerosol particles or a predetermined range of aerosol particle sizes to pass therethrough for inhalation. For example, an optional secondary filter can be used within a downstream cavity or on the downstream end to control the mass flow of aerosol particles for inhalation, or further control the size of the aerosol particles for inhalation.

Preferably, the upstream filter 110 has a smaller mesh or porosity than the downstream filter 140 to allow aerosol particles to pass through the downstream filter and not pass through the upstream filter. Also preferably, the secondary filter has a smaller mesh or porosity than the downstream filter 140 to further filter or control the sizes of the aerosol particles prior to inhalation.

Figure 4:
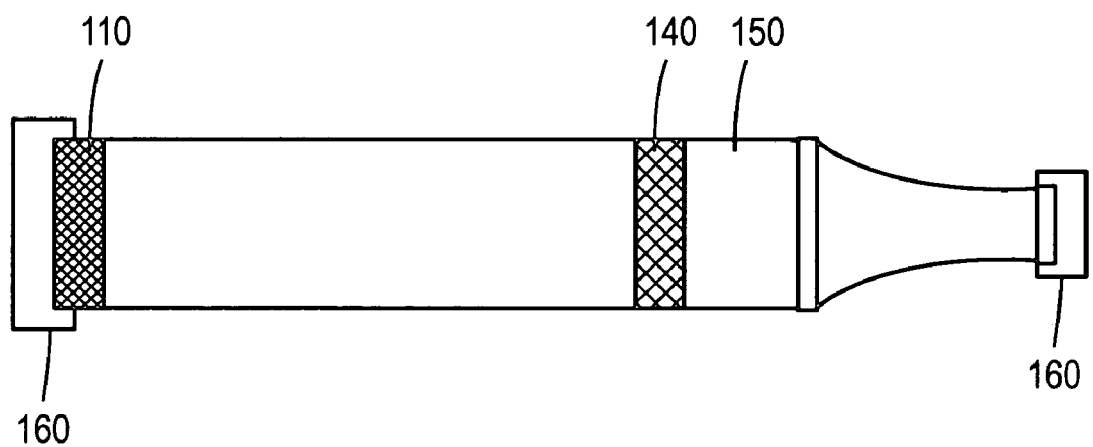
FIG. 4 illustrates another exemplary embodiment of a method of aerosolizing a powder for inhalation.

Also, it is noted that one or more optional end caps 160 can be provided to prevent powder loss out from the upstream end 101 (FIG. 2A) and/or the downstream end 102 (FIG. 1), as illustrated in FIG. 4.

As provided herein, aerosolizable powder can be provided downstream from the upstream filter within a cavity of a device. By providing the aerosolizable powder in a central cavity of the hollow device, release of the powders and the aerosol particles can be controlled by the filters, as well as one or more end caps 160.

The aerosolizable powder is preferably sized to provide sufficient levels of taste and/or aerosol delivery of a predetermined substance within the device, and to allow for sufficient movement between the powder pieces to allow for mechanical energy to be passed to the powder pieces and allow for the powder to be aerosolized. Thus, the aerosolizable powder should be small enough to fit within a hollow device, but large enough to provide sufficient amounts of substance for aerosolization.

In an exemplary embodiment, the substance in aerosolizable powder form can be up to 4 millimeters in at least one dimension prior to aerosolization. By providing aerosolizable powder that is up to 4 millimeters, multiple individual powder pieces can fit within the device, and should not pass through the filters prior to impact between the powder pieces by agitation of the device. Additionally, such sizing can allow for space to be provided between powder pieces to allow the powder pieces to move within the device 100 and impact with other powder pieces, the device, and the filters.

The aerosolizable powder exclusive of the aerosol particles can be any size at least as large as the aerosol particles. In exemplary embodiments, the aerosolizable powder is sized greater than about 1.0 mm in at least one dimension. For example, the aerosolizable powder can have at least one dimension between about 1.0 and about 4.0 millimeters if larger aerosolizable powder 120 is desired, wherein the aerosolizable powder may appear as a solid bead. Alternatively, the aerosolizable powder can have at least one dimension between about 10 and about 30 microns if smaller aerosolizable powder 310 is desired, wherein the aerosolizable powder may appear as small particles. As a second alternative, the aerosolizable powder can be include particles sized between about 10 and about 30 microns agglomerated into powder sized greater than about 1.0 mm in one dimension or between about 1.0 mm and about 4.0 mm in one dimension, wherein the aerosolizable powder may appear as an agglomeration of small particles. It is noted that combinations of these differently sized aerosolizable powders can also be provided.

By providing larger aerosolizable powder, aerosol particles can be formed therefrom by breaking-off or loosening particles from the larger aerosolizable powder, wherein the aerosolizable powder is still confined within the device by the filters and the walls of the device. Alternatively, if smaller aerosolizable powder is provided within a hollow device, aerosol particles can be formed by deagglomerating aggregated aerosolizable powder or freeing particles for inhalation or ejection from the downstream filter.

Upon aerosolization, the aerosolizable powder provided should be capable of forming aerosol particles from about 10 to about 30 micrometers in at least one dimension for oral or taste delivery. In an exemplary embodiment, aerosol particles are at least 10 micrometers, as this allows delivery of the aerosol particles into a mouth of a consumer, while avoiding or minimizing delivery to the lower airways of the lungs. Additionally, it is preferable that the aerosol particles be at most about 30 micrometers to avoid large particles from causing discomfort (i.e., large granules in the mouth) by large particle impaction against surfaces of a mouth upon inhalation.

Additionally, the aerosolizable powder can include one or more flavorants, including any natural or synthetic flavor, extract, oil or aroma, such as tobacco, smoke, menthol, mint (e.g., peppermint and spearmint), chocolate, licorice, fruit flavors (e.g., lemon and strawberry), vanilla, vanillin, ethyl vanillin, breath freshener flavors, spice flavors (e.g., cinnamon and cloves), methyl salicylate (e.g., wintergreen), linalool, bergamot oil, geranium oil, and ginger oil.

The aerosolizable powder can be in the form of solid powder pieces (e.g., large or small pellets; or large or small agglomerations of particles) with the one or more substances throughout the mass of each powder piece or can include coatings or layers of flavor and/or chemicals on carriers. For example, the aerosolizable powder can include solid, coated or encapsulated powders, including but not limited to one or more of the following substances or combinations thereof: lactose, glucose, or other sugars, flavors, and salt or other excipients to aid stability and aerosolizibility.

Also, in an exemplary embodiment, aerosolizable powder is frangible and can be broken from larger powder pieces (or previously broken larger powder pieces) to form a combination of broken larger aerosolizable powder pieces and aerosol particles.

The aerosolizable powder is preferably sufficiently weak and brittle such that the aerosolizable powder can be broken with moderate force from consumer-induced mechanical agitation or shaking. However, the aerosolizable powder is preferably sufficiently strong and ductile to reduce breakage of the aerosolizable powder during transport and/or storage of the device.

As mentioned above, secondary powder can be provided to impact with aerosolizable powder to break the aerosolizable powder into small aerosol particles. The secondary powder can be any material with a hardness level of at least equivalent to the aerosolizable powder, which is safe for oral inhalation and non-volatile. Hardness of the secondary powder is desired to aid in aerosolizing the aerosolizable powder into aerosol particles by transferring mechanical energy from agitating the device to create aerosol particles from broken off pieces of the aerosolizable powder.

Similar to the aerosolizable powder, the secondary powder can also be greater than about 1.0 mm in one dimension or between about 1.0 and about 4.0 millimeters in one dimension for providing a large enough impact surface to interact with the aerosolizable powder, yet small enough to allow for movement within the device. For example, rice, alumina, silica, sugar, and/or salt particles with at least one dimension ranging from about 2.0 to about 4.0 millimeters can be used as the secondary powder.

Preferably, the aerosolizable powder has a hardness of less than or equal to the secondary powder, such that the secondary powder can transfer mechanical energy through impact with the aerosolizable powder. The level of the transfer of mechanical energy can be chosen to be sufficient to cause breakage of the aerosolizable powder with or without breakage of the secondary powder. In an exemplary embodiment, the secondary powder is about 2.0 to about 4.0 millimeters (and any 0.1 value in between this range) in at least one dimension and can be about the same size as the aerosolizable powder prior to mechanical agitation breakage of the aerosolizable powder.

A hollow device is preferably used to house the powders. Preferably, the hollow device can provide structural integrity (e.g., the resistance to crushing and bending) to the device. As such, the hollow device can be any container, such as a hollow, elongated device, to contain the powders and particles therein. In an exemplary embodiment, a hollow, elongated device has a transverse dimension of about 3.0 to about 8.0 millimeters (and any 0.1 value in between this range), wherein the hollow, elongated device is sized to be portable and convenient for handling. In one exemplary embodiment, the hollow device is shaped to look and feel like a cigarette, and the device can be used as a smoking substitute device.

The hollow device also preferably provides axial and radial structural integrity to the device, as well as sufficient strength to withstand agitation and impact by the aerosolizable powder and the secondary powder. In order to provide structural integrity, the hollow device is preferably shaped in a cylindrical, tubular shape and can be made of a polymer, a paper, a metal, an alloy, or a combination thereof.

Additionally, a cover or enclosure can also be provided to protect the device from damage. An exemplary embodiment can include but is not limited to a plastic, fabric or metal enclosure to protect the device.

Therefore, a preferable method of producing or delivering aerosol particles can include agitating an aerosolizable powder and a secondary powder in a hollow device to aerosolize the powder into aerosol particles. Preferably, the agitating deagglomerates or breaks up the aerosolizable powder into aerosol particles. Additionally, in order to provide the aerosol particles to a consumer, it is also preferable to allow for air to pass through an upstream end of the hollow device so as to remove the aerosol particles from a downstream end of the hollow device.

In addition to producing or delivering aerosol particles, also preferably provided is a method of making an aerosol delivery device. In order to make an exemplary aerosol delivery device, preferably a hollow, elongated device is provided and filled with an aerosolizable powder and a secondary powder. By providing the two simultaneously, the production for the aerosol delivery device may be simplified with a single filling step. It is noted however that more than the two powders can be used, and more than a single filling step can also be used depending upon the process used.

After providing the powders within the device, an upstream portion and a downstream portion of the device can be sealed. Preferably, the device is sealed using filters or the like in order to confine powders within the device. At this point, optional end caps over the upstream and downstream portions can be provided in addition to the filters. Alternatively, the device can be wrapped or encased in a wrapper or the like to further seal the powders within the device and to prevent loss of aerosol particles.

Also provided is an aerosol delivery device kit of component parts capable of being assembled. By providing the aerosol delivery device as a kit, parts of the aerosol delivery device can be replaced or reused as desired. An exemplary kit can include a hollow device, powder including an aerosolizable powder, and filters. Similar to the aerosol delivery device described above, the powder provided with the kit is preferably adapted to produce aerosol particles within the hollow device. Additionally, the kit preferably includes powder with at least a portion of the aerosol particles being the same material as the aerosolizable powder, with a secondary powder provided to be harder than the aerosolizable powder. Preferably, the powder in the kit is adapted to be positioned within the device between upstream and downstream filters, which may be positioned on the upstream and downstream end portions of the device to contain the powder within the hollow device.

Variations and modifications of the foregoing will be apparent to those skilled in the art. For example, additional air inlets can be provided at positions along the length of the device to increase airflow or adjust the resistance to draw if desired. Additionally, more than two powders can be used in the device. For example, three aerosolizable powders (e.g., an aerosolizable tobacco-flavored powder, an aerosolizable mint-flavored powder, and an aerosolizable menthol-flavored powder) can be provided along with a hard salt, non-aerosolizable powder can be provided in a device. Such variations and modifications are to be considered within the purview and scope of the claims appended hereto.

What is claimed is:

1. An aerosol powder delivery device, comprising:
   a hollow device;
   aerosolizable powder adapted to produce aerosol particles within the hollow device, wherein at least a portion of the aerosol particles comprise the same material as the aerosolizable powder;
   a secondary powder within the hollow device, wherein at least a portion of the aerosolizable powder, the secondary powder, or both are about 1.0 mm to about 4.0 mm in at least one dimension,
   an upstream filter adapted to prevent escape of the aersolizable powder and the secondary powder from the hollow device;
   a downstream filter adapted to prevent escape of the aerosolizable powder and the secondary powder from the hollow device; and
   a secondary filter positioned adjacent to the downstream filter and adapted to control the size of aerosol particles passing therethrough.

2. The device of claim 1, wherein the upstream filter allows air to pass through the upstream filter and into the hollow device, and wherein the upstream filter optionally comprises a polymeric foam, a honeycomb filter, a screen, or a cigarette filter material.

3. The device of claim 1, wherein the downstream filter allows aerosolized particles to pass through the downstream filter, and wherein the downstream filter optionally comprises a polymeric foam, a honeycomb filter, a screen, or a cigarette filter material.

4. The device of claim 3, wherein the secondary filter further filters the aerosolized particles passing through the downstream filter, and wherein the secondary filter optionally comprises polymeric foams, a honeycomb filter, a screen, or a cigarette filter material.

5. The device of claim 1, wherein the secondary powder is harder than the aerosolizable powder, and wherein at least a portion of the aerosolizable powder is between about 1.0 and about 4.0 millimeters in at least one dimension, at least a portion of the secondary powder is between about 2.0 and about 4.0 millimeters in at least one dimension, and at least a portion of the aerosol particles is between about 10 and about 30 micrometers in at least one dimension.

6. The device of claim 1, wherein the aerosolizable powder is a solid or a coated powder comprising: lactose, glucose, flavor, or a combination thereof, and/or wherein the secondary powder comprises particles harder than the aerosolizable powder.

7. The device of claim 1, wherein the hollow device is a hollow, elongated body and/or wherein the hollow device comprises polymer, paper, metal, alloy, or combination thereof.

8. The device of claim 1, wherein the hollow device contains beads of the aerosolizable powder which are softer than beads of the secondary powder, and wherein the aerosolizable powder and secondary powder are adapted to be broken apart to form aerosol particles by shaking the hollow device with the aerosolizable powder and the secondary powder therein to break and/or deagglomerate the aerosolizable powder into aerosol particles.

9. A method of producing or delivering aerosol particles, comprising steps of:
- agitating an aerosolizable powder and a secondary powder in a hollow device to aerosolize the aerosolizable powder into aerosol particles; and
- passing air through an upstream filter of the hollow device so as to remove the aerosol particles from a downstream end of the hollow device through a downstream filter and a secondary filter positioned adjacent the downstream filter and adapted to control the size of aerosol particles passing therethrough.

10. The method of claim 9, wherein the agitating causes the aerosolizable powder to break into the aerosol particles.

11. The method of claim 9, wherein the agitating an aerosolizable powder and a secondary powder in a hollow device aerosolizes the aerosolizable powder into aerosol particles of between about 10 micrometers and about 30 micrometers in at least one dimension.

12. A method of making an aerosol delivery device, comprising:
- filling a hollow device with an aerosolizable powder and a secondary powder, wherein at least a portion of the secondary powder and the aerosolizable powder are larger than about 1.0 mm in at least one dimension; and
- sealing an upstream portion and a downstream portion of the hollow device using an upstream filter, a downstream filter and a secondary filter, wherein the aerosolizable powder and the secondary powder are confined within the hollow device between the upstream filter and the downstream filter and the secondary filter is adjacent the downstream filter.

13. The method of claim 12, wherein the filling of the hollow device with an aerosolizable powder and a secondary powder comprises filling the hollow, device with an aerosolizable powder with at least one dimension between about 1.0 and about 4.0 millimeters, and a secondary powder with at least one dimension between about 2.0 and about 4.0 millimeters.

14. The method of claim 12, wherein the filling of the hollow device with an aerosolizable powder and a secondary powder comprises filling a hollow device with a solid, a coated and/or an encapsulated aerosolizable powder comprising: lactose, glucose, flavor, or a combination thereof, and a secondary powder, wherein the secondary powder is harder than the aerosolizable powder.

15. An aerosol delivery device kit of component parts capable of being assembled, comprising:
- a hollow device;
- powder including an aerosolizable powder adapted to produce aerosol particles within the hollow device, wherein at least a portion of the aerosol particles comprise smaller particles of the same material as the aerosolizable powder, and a secondary powder within the hollow device, wherein at least a portion of the aerosolizable powder, the secondary powder, or both are at least about 1.0 mm in at least one dimension, wherein the powder is adapted to be positioned within the hollow device;
- upstream and downstream filters, whereby the upstream and downstream filters may be positioned on the upstream and downstream end portions, respectively, of the hollow device to contain the powder within the hollow device, and
- a secondary filter positioned adjacent to the downstream filter and adapted to control the size of aerosol particles passing therethrough.

16. The kit of claim 15, wherein the powder comprises solid, encapsulated or coated powders comprising: lactose, glucose, a flavor, rice, alumina, silica, or combination thereof.

17. The kit of claim 15, wherein the hollow device is a hollow, elongated device and/or wherein the hollow device comprises polymer, paper, metal, alloy, or combination thereof.

18. The kit of claim 15, wherein at least a portion of the aerosolizable powder is between about 1.0 and about 4.0 millimeters in at least one dimension, at least a portion of the secondary powder is between about 2.0 and about 4.0 millimeters in at least one dimension, and at least a portion of the aerosol particles is between about 10 and about 30 micrometers in at least one dimension.

19. The kit of claim 15, wherein the upstream and downstream filters comprise polymeric foams, honeycomb filters, screens, or cellulose acetate, and wherein the downstream filter passes aerosol particles therethrough.

20. The kit of claim 15, further comprising one or more end caps adapted to be positioned on one or both ends of the hollow device.

* * * * *